US012496231B1

(12) United States Patent
Johnson

(10) Patent No.: US 12,496,231 B1
(45) Date of Patent: Dec. 16, 2025

(54) TREATMENT SYSTEM FOR POST MARINE ENVENOMATION

(71) Applicant: Daniel W Johnson, San Diego, CA (US)

(72) Inventor: Daniel W Johnson, San Diego, CA (US)

( * ) Notice: Subject to any disclaimer, the term of this patent is extended or adjusted under 35 U.S.C. 154(b) by 772 days.

(21) Appl. No.: 17/848,351

(22) Filed: Jun. 23, 2022

Related U.S. Application Data

(60) Provisional application No. 63/214,064, filed on Jun. 23, 2021.

(51) Int. Cl.

*A61F 13/05* (2024.01)
*A61F 13/00* (2006.01)
*A61F 17/00* (2006.01)

(52) U.S. Cl.

CPC ........ *A61F 13/05* (2024.01); *A61F 13/00063* (2013.01); *A61F 17/00* (2013.01)

(58) Field of Classification Search

CPC ..... A61F 13/05; A61F 13/00063; A61F 17/00
See application file for complete search history.

(56) References Cited

U.S. PATENT DOCUMENTS

| | | | | |
|---|---|---|---|---|
| 2005/0091880 | A1 * | 5/2005 | Harris | A61H 35/006 36/2.6 |
| 2009/0004433 | A1 * | 1/2009 | Privitera | B32B 27/36 428/339 |
| 2020/0170770 | A1 * | 6/2020 | Orr | A61F 7/10 |

OTHER PUBLICATIONS

NHS (https://www.nhs.uk/conditions/jellyfish-and-other-sea-creature-stings/), available 2019 (Year: 2019).*

* cited by examiner

*Primary Examiner* — Andrew S Rosenthal

(74) *Attorney, Agent, or Firm* — Plager Schack LLP; Mark H. Plager; Naomi Mann

(57) ABSTRACT

A system for treating an injured area of a limb comprises inserting the limb into a pocket of a limb receiving device; pouring a sterile liquid into the pocket to submerge the injured area; and activating a chemical exothermic reaction between two or more flameless reactive components within a heating compartment of the limb receiving device, wherein the heating compartment is in thermal contact with the pocket, and wherein the chemical reaction generates heat for heating the sterile liquid within the pocket.

9 Claims, 3 Drawing Sheets

TREATMENT SYSTEM FOR POST MARINE ENVENOMATION

RELATED APPLICATION

This application claims benefit to U.S. Provisional Application No. 63/214,064 filed Jun. 23, 2021, which is incorporated by reference herein in its entirety

BACKGROUND

The present disclosure relates generally to systems for treatment of marine envenomation.

Envenomation by marine creatures is becoming increasingly common. The discomfort associated with marine envenomation as well as its comorbidity and rare mortality are significant concerns for the seagoing public. As such, there is a need for an improved system for treatment of marine envenomation.

SUMMARY

According to various embodiments, disclosed is a system for treating an injured area of a limb, wherein the injury may be due to marine envenomation. In embodiments, the system may comprise inserting the limb into a pocket of a limb receiving device; pouring a sterile liquid into the pocket to submerge the injured area; and activating a chemical exothermic reaction between two or more flameless reactive components within a heating compartment of the limb receiving device, wherein the heating compartment is in thermal contact with the pocket, and wherein the chemical reaction generates heat for heating the sterile liquid within the pocket.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Marine envenomation injury may often result in significant pain and/or infection. Application of a heated sterile solution along with foreign body removal is a commonly used treatment to address such injuries. However, providing prompt treatment when on a boat, remote shoreline, other outdoor environment where the injury occurs, or in route to a care facility, may be unfeasible or impractical for the unprepared individual. In many instances, the victim may be forced to wait in considerable pain for a sterile solution to be heated to an effective temperature and/or until other effective treatment may be rendered. This prolongs pain and delays the antiseptic procedures required to prevent a comorbid infection common with marine envenomation and other foreign body puncture wounds.

Figure 1:
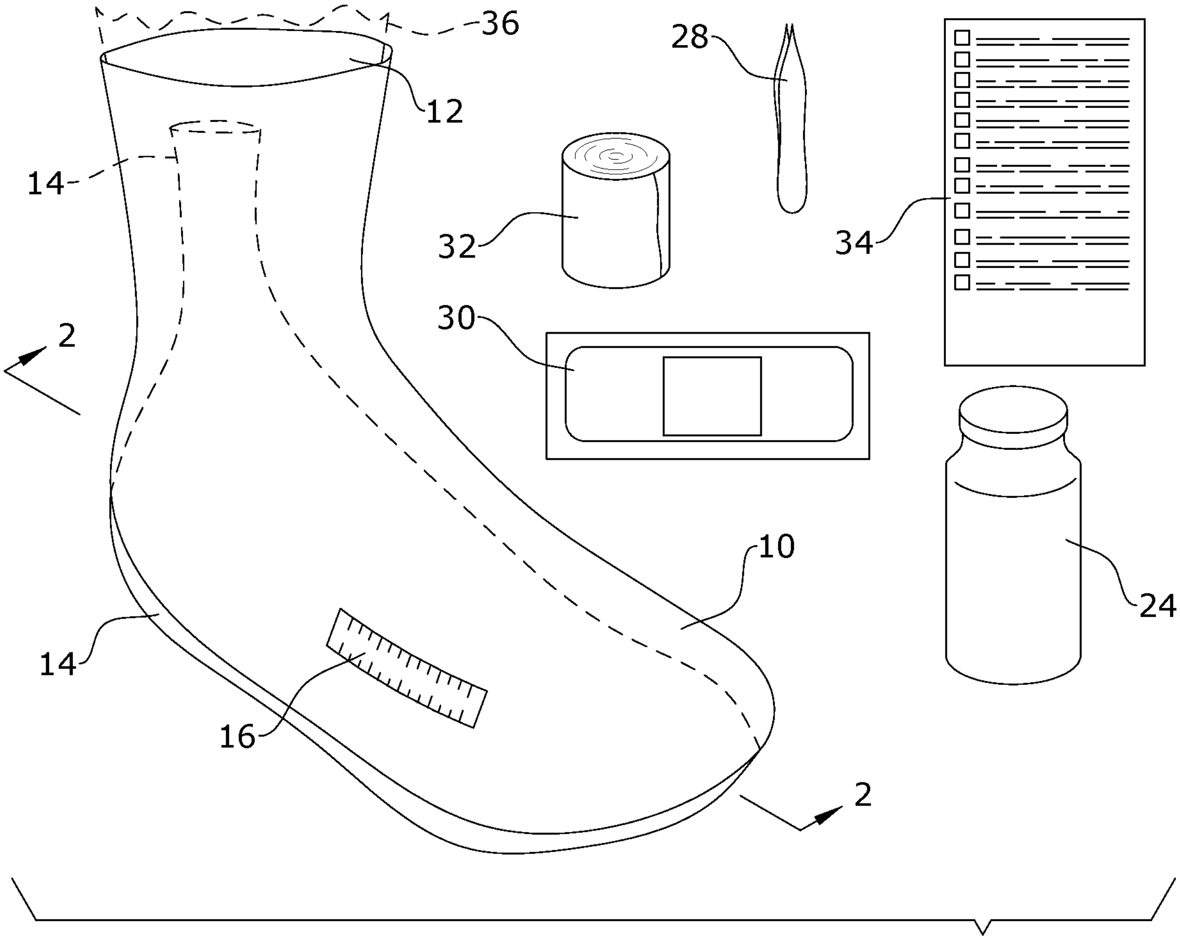
FIG. 1 is a schematic view of a kit comprising a limb receiving device for the treatment of envenomation or other injury, in accordance with certain embodiments.
Figure 2:
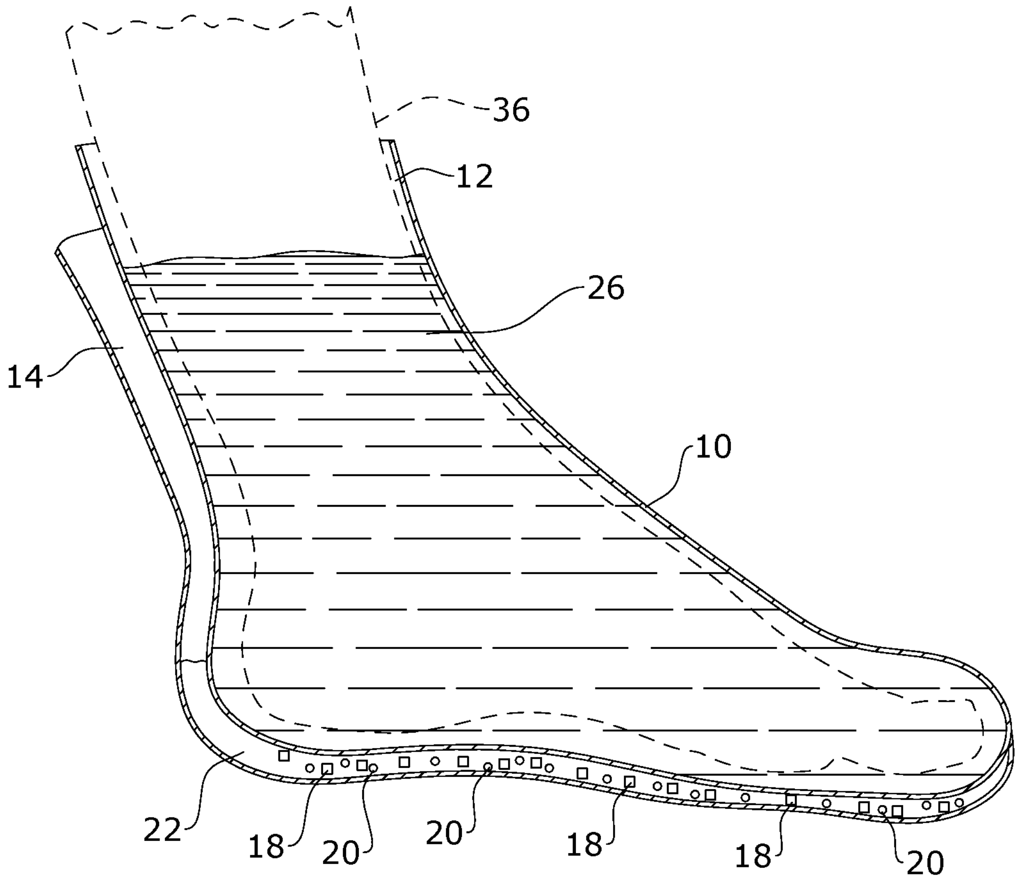
FIG. 2 is a section view of the limb receiving device taken along line 2-2 of FIG. 1.
Figure 3:
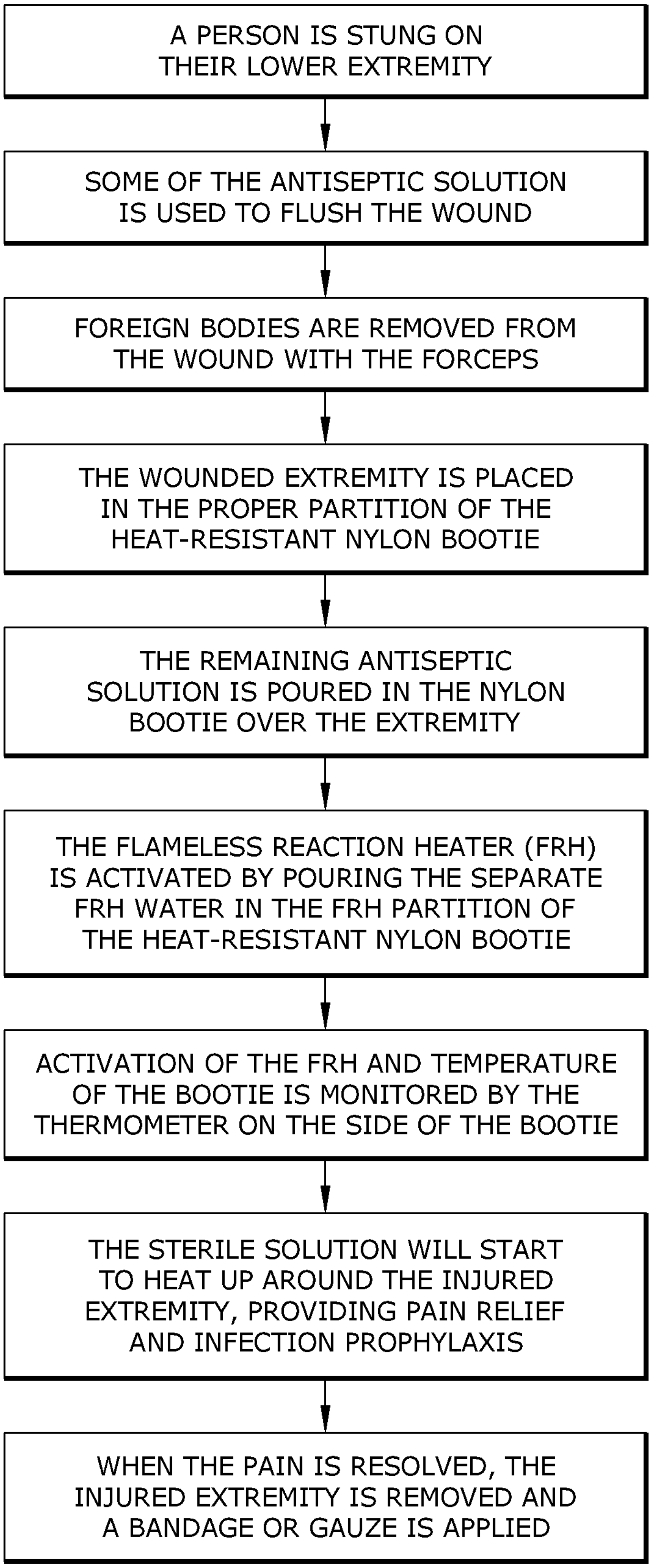
FIG. 3 is a flow chart for a method of treatment of injury caused by envenomation.

According to various embodiments as depicted in FIGS. 1-3, the disclosed subject matter introduces a treatment system which is portable and may be used in any setting to provide immediate and effective treatment for envenomation injury. In embodiments, the disclosed system uses an extremity receiving device which provides a pocket for a sterile solution and the limb, and which further includes a heating compartment in thermal contact with the pocket and which utilizes a heat generating chemical exothermic reaction to effectively heat the sterile solution.

In certain embodiments as best depicted in FIGS. 1 and 2, the disclosed system provides a limb receiving device 10 configured to receive a limb or extremity 36 of the body, such as a foot, hand, or lower part of the leg or arm. In embodiments, device 10 may generally include a main pocket 12 configured to contain limb 36 along with an antiseptic and/or sterile solution 26. Device 10 may further include a heating compartment 14 formed around at least a portion of pocket 12. In further embodiments, device 10 may also include a thermometer 16. In some embodiments, pocket 12 and heating compartment 14 may be waterproof and heat resistant. Additionally, pocket 12 and heating compartment 14 are preferably flexible to allow freedom of movement. It shall be appreciated however that pocket 12 and/or heating compartment 14 may be rigid in alternate embodiments. In one embodiment, pocket 12 and heating compartment 14 may be made of nylon. It shall be appreciated that other materials or combination of materials may be used in alternate embodiments. In further embodiments, the disclosed system may use insulative material(s) for prevention of surface heat loss, and/or conductive material (s) for effective heat transfer between the heating compartment and pocket.

In some embodiments, pocket 12 may be specifically configured for receiving a certain extremity. For example, pocket 12 may be configured as a bootie for receiving a foot and lower part of the leg, as shown in the figures. In other embodiments, pocket 12 may be configured as a glove/mitten for receiving a hand and arm. In further embodiments, pocket 12 may be sized to fit a specific group of individuals (e.g., children, adults, small, medium, large, etc.). In alternate embodiments, pocket 12 may be generically sized and shaped to accommodate any extremity and a range of different sizes.

In embodiments, heating compartment 14 may be formed adjacent to pocket 12, and in thermal contact therewith. Additionally, heating compartment 14 forms a separate enclosure configured to contain a liquid solution. In some embodiments, heating compartment 14 may extend over a portion of pocket 12. In one example, heating compartment 14 may extend over a back and bottom foot portion of a bootie type pocket as shown in the figures. In other embodiments, heating compartment 14 may extend over the entire or the majority of the surface of pocket 12. In some other embodiments, device 10 may comprise multiple heating compartments 14, which extend over different portions of pocket 12. For example, one heating compartment 14 may extend over a back/bottom portion of pocket 12, and another heating compartment 14 may extend over a front portion of pocket 12.

In embodiments, the disclosed system may utilize a flameless reactive heating (FRH) system comprising two or more reactive components configured to produce a chemical reaction that generates heat within heating compartment 14. In certain embodiments, the FRH system may comprise an activation fluid 22 which may be water, and aluminum 18 and sodium hydroxide 20 which may be in solid form. In one embodiment, these ingredients may be mixed in proportion of approximately 6 parts water to approximately 2 parts elemental aluminum to approximately 2 parts sodium hydroxide. In some embodiments, the aluminum and sodium hydroxide ingredients may be prestored within heating compartment 14, leaving the user with the task of pouring in the activation fluid to initiate the heat generating reaction. In other embodiments, all ingredients may be stored outside of heating compartment 14 and may be poured into the compartment for use. Additionally, all ingredients may be provided in premeasured amounts for providing a desired temperature based on such factors as the size of device 10, material(s) and/or heat transfer characteristics of the device, anticipated needs of the user, etc. In certain embodiments, the FRH system may be configured to heat solution 26 to a temperature of approximately 47.7 degrees Celsius or 118 degrees Fahrenheit. It shall be appreciated that different FRH system components and/or quantities of various components may be provided in alternate embodiments. Additionally, other metal powders such as magnesium or iron, may be used instead of aluminum in alternate embodiments. As an example, a reaction between magnesium powder and water may be used in alternate embodiments.

In certain embodiments, thermometer 16 may be coupled to or embedded within a portion of device 10, such as pocket 12 (as shown in the figures) or compartment 14 and is configured to measure the temperature rise due to activation of the FRH reactive components. In other embodiments, thermometer 16 may be separate or removable from device 10. In certain embodiments, device 10 may comprise more than one thermometer.

In certain embodiments and with particular reference to FIG. 1, the disclosed system may be provided as a portable treatment kit, which includes at least one device 10, and may further include at least one container 24 that holds antiseptic solution 26, and at least one other container which holds activation fluid 22. In certain embodiments, a premeasured amount of the activation fluid 22 may be provided for mixing with the flameless reactive components. In some embodiments, the antiseptic solution 26 may itself be water. According to an exemplary embodiment, container 24 may be filled with approximately 250 ml of sterile saline or water 250 ml, and the activation fluid container may be filled with approximately 100 ml of water. In some embodiments, the portable treatment kit may further include items such as forceps 28 for foreign body removal, bandages 30 which may be used to cover and protect a wound resulting from envenomation, a roll of gauze 32, and instructions/procedure checklist 34, etc. In certain embodiments, the treatment kit may also include such items as an epinephrine autoinjector, topical and/or oral antibiotics, and the like. The treatment kit may be used by any individual, first responder, medical professional, etc., and may be conveniently stored in a travel bag, beach bag, tackle box, and the like for providing a portable and rapid heating system for treatment of an injury.

With particular reference to FIG. 3, a method for treatment of an envenomated area using device 10 and/or the above-described treatment kit may comprise inserting the affected extremity 36 in the pocket 12 of device 10, then activating the flameless reactive components within heating compartment 14. In some embodiments, antiseptic/sterile solution 26 may be poured into pocket 12 for submersion of the injured area. This step may preferably be performed after placement of extremity 36 within pocket 12. In some embodiments, the wounded area may also be flushed with the sterile solution prior to inserting it into the device. In certain embodiments, the injured area may be checked for any foreign body (e.g., a stinger), which may be removed using forceps 28 provided within the treatment kit. In certain embodiments, activating the flameless reactive system may comprise pouring water into heating compartment 14 to activate reactive ingredients which are prestored in the pocket. This step may preferably be performed after the sterile solution has been poured into pocket 12. In further embodiments, once the flameless reactive heating ingredients have been activated, a user may monitor the temperature of device 10 using thermometer 16. As the sterile solution heats up around the injured extremity, it effectuates pain relief and infection prophylaxis. Additionally, as the disclosed system is applied to a large area and not just a single location, it may provide effective relief in case of multiple stings to an extremity. Once the pain is resolved, the user may remove the injured extremity and examine or re-examine it for any foreign body then apply a bandage or gauze to the wounded area if needed.

As the disclosed system does not require a flammable nor electrical heat source which may be difficult to procure and/or control in an outdoor or marine environment, it may be applied immediately to address pain and prevent other possible injuries such as infections, sequelae related to potential delay in treatment, morbidity, and even mortality from envenomation.

The disclosed system may be used for rapid and effective treatment of envenomation and various types of injury including, but not limited to, penetrating fish stings, surface stings, puncture type stings, and the like. It shall be appreciated that the disclosed system may be used to treat envenomation/injury by marine creatures (e.g., stingray/Chondrichthyes, sea urchin/echinoderms, scorpionfish, lionfish, /Scorpaena, etc.) as well as non-marine creatures (e.g., spiders, scorpions, bees, ants, etc.) in alternate embodiments. It shall further be appreciated that the disclosed system may be used for treatment of other types of injuries and/or medical conditions which may benefit from the application of heat. While the disclosed system may apply to the treatment of humans, it may also be used to treat animals in alternate embodiments.

It shall be appreciated that the disclosed system can have multiple configurations in different embodiments. In certain embodiments, the disclosed system may be configured for use with other body parts, by providing a sleeve with an open end that seals against a portion of the body to hold in the sterile solution. In some embodiments, the disclosed system may provide a software application and/or audible instructions (similar to an automatic defibrillator) which may guide an individual in following the proper treatment protocol and/or monitor the health status of the affected individual.

It shall be appreciated that the components of the system described herein may comprise any alternative known materials in the field and be of any size and/or dimensions. It shall be appreciated that the components of the system described herein may be manufactured and assembled using any known techniques in the field.

The constituent elements of the disclosed device and system listed herein are intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. Terms such as 'approximate' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method for treating an injured area on a limb, the method comprising:

inserting the limb into a pocket of a limb receiving device;

pouring a sterile liquid into the pocket to submerge the injured area; and activating a chemical reaction between two or more flameless reactive components within a heating compartment of the limb receiving device, wherein the heating compartment is in thermal contact with the pocket, and wherein the chemical reaction generates heat for heating the sterile liquid within the pocket, wherein the method is applied to envenomation and/or sting injury caused by a marine creature, wherein the limb receiving device is a component of a kit for treatment of injury in an outdoor marine environment, wherein the two or more flameless reactive components are provided in pre-measured amounts that are suitable for activating said chemical reaction and for generating heat sufficient to treat said envenomation and/or sting injury, and wherein neither a flammable nor an electrical heat source is used for heating the sterile liquid.

2. The method of claim 1, wherein the limb receiving device further comprises a thermometer.

3. The method of claim 1, wherein activating the chemical reaction comprises pouring an activation fluid into the heating compartment, wherein the heating compartment contains the remaining reactive component(s).

4. The method of claim 3, wherein the activation fluid is liquid, and wherein the remaining reactive components are aluminum and sodium hydroxide.

5. The method of claim 1, further comprising flushing the injured area with a sterile solution and/or removing a foreign body from the injured area when the limb is outside of the pocket.

6. A kit for treating an injured area on a limb, the system comprising:

a limb receiving device comprising a pocket and a heating compartment in thermal contact with the pocket, the pocket being configured to receive the limb together with a liquid; and two or more flameless reactive components configured to generate heat within the heating compartment upon chemically reacting, wherein the kit is indicated for treatment of an envenomation and/or sting injury caused by a marine creature in an outdoor environment, wherein the two or more flameless reactive components are provided in pre-measured amounts that are suitable for generating heat sufficient to treat said envenomation and/or sting injury without the need for an additional heat source.

7. The kit of claim 6, wherein at least a portion of the flameless reactive components is preloaded within the heating compartment, wherein the kit further comprises a liquid activation agent configured to initiate a chemical exothermic reaction when poured into the heating compartment comprising the flameless reactive components.

8. The kit of claim 7, further comprising a sterile solution for pouring into the pocket and/or for cleaning the injured area.

9. The kit of claim 6, wherein the limb receiving device further includes a thermometer coupled to the pocket.

* * * * *